(12) United States Patent
Kasai

(10) Patent No.: US 7,724,430 B2
(45) Date of Patent: May 25, 2010

(54) RIGID ENDOSCOPE

(75) Inventor: Ken Kasai, Shibuya-Ku (JP)

(73) Assignee: Olympus Medical Systems Corp., Tokyo (JP)

( * ) Notice: Subject to any disclaimer, the term of this patent is extended or adjusted under 35 U.S.C. 154(b) by 8 days.

(21) Appl. No.: 12/218,782

(22) Filed: Jul. 17, 2008

(65) Prior Publication Data

US 2010/0014161 A1    Jan. 21, 2010

(51) Int. Cl.
*G02B 23/24* (2006.01)
(52) U.S. Cl. ............................. 359/434; 600/101
(58) Field of Classification Search ............ None
See application file for complete search history.

(56) References Cited

U.S. PATENT DOCUMENTS 4,693,568 A * 9/1987 Takahashi ................ 359/772
5,005,960 A * 4/1991 Heimbeck ................ 359/435
2009/0108232 A1* 4/2009 Kumatoriya et al. ... 252/182.32

FOREIGN PATENT DOCUMENTS

JP           2002-202403           7/2002
WO    WO 2005049897 A1 *    6/2005

OTHER PUBLICATIONS

English machine translation of JP2002-202403.*

* cited by examiner

*Primary Examiner*—Lee Fineman
(74) *Attorney, Agent, or Firm*—Kenyon & Kenyon LLP

(57) ABSTRACT

The invention provides a rigid endoscope relay optical system that can be fabricated at lower costs while its brightness is kept intact by reducing parts count. The rigid endoscope optical system has an elongate insert and is adapted to implement image transfer using relay lenses Re1 to Re7. The relay lenses Re1 to Re7 each have at least two rod lenses and satisfy nd>2, where nd stands for the refractive index on d-line basis of each rod lens in the relay lens.

3 Claims, 13 Drawing Sheets

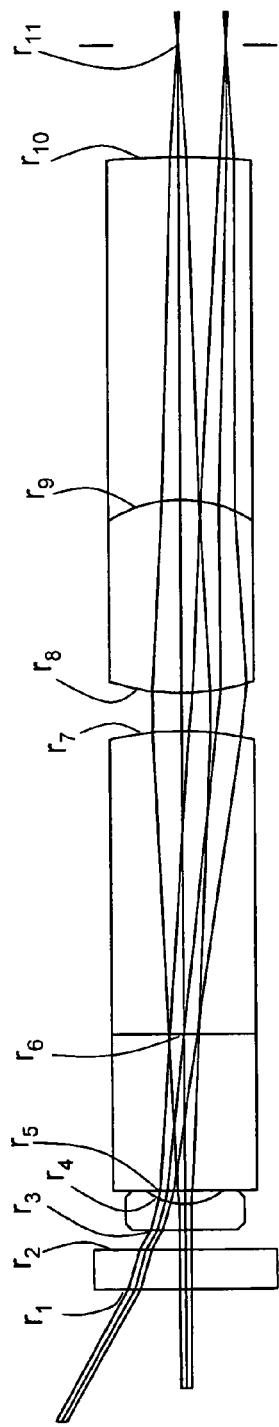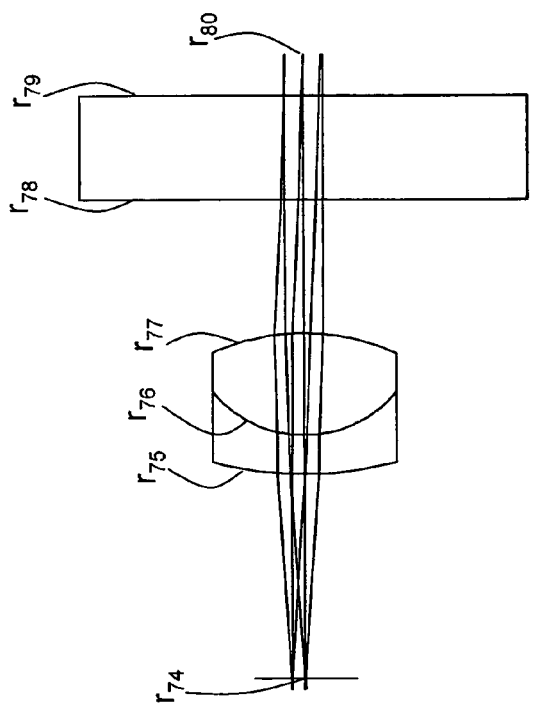
FIG. 4(a)
FIG. 4(b)

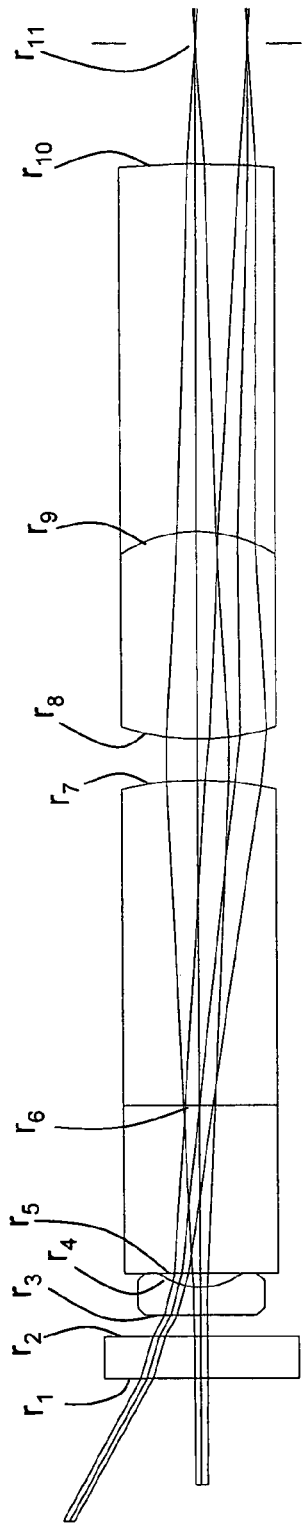
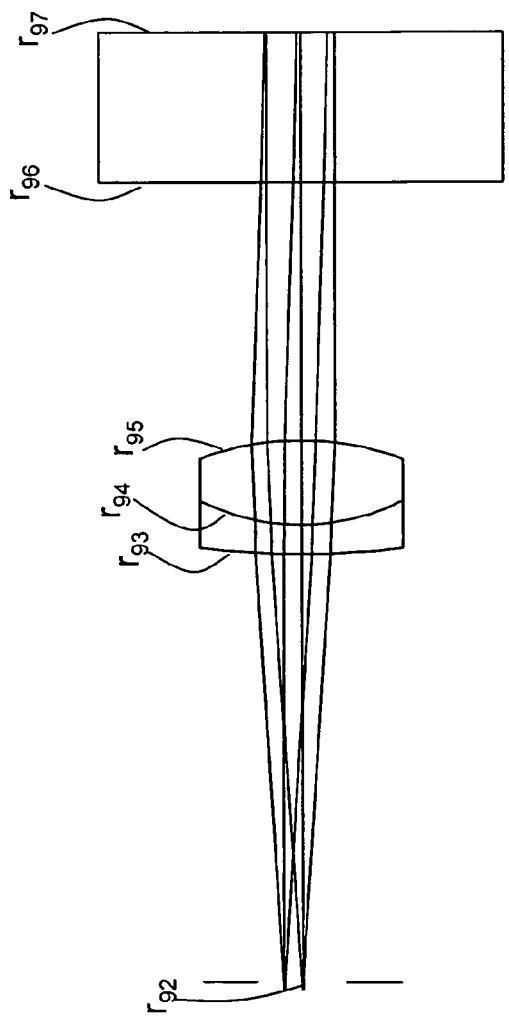
FIG. 13(a)
FIG. 13(b)

RIGID ENDOSCOPE

BACKGROUND OF THE INVENTION

The present invention relates to a rigid endoscope and an image transfer optical system for that rigid endoscope.

A viewing optical system for the rigid endoscope generally comprises a relay optical system adapted to transfer images formed through an objective lens to a viewer side wherein an elongate rod lens is used to relay the image odd-numbered times.

A rigid endoscope for the urinary organs of infants and little children has an insert of about $\phi 3$ mm. In the industry fields, there is an ultra-fine rigid endoscope having an insert diameter of about $\phi 1$ mm to 3 mm that is used for the inside observation or the like of automotive engines.

In order for the fine-diameter rigid endoscope to gain brightness, it is required to implement a lot more relays with an increased NA (numerical aperture).

With a typical prior art endoscope having a lens outer diameter of $\phi 1.1$ mm and a total relay length of about 230 mm, nine relays are implemented to achieve NA=0.068.

With such prior arts, however, there are the following problems. As nine relays are implemented with 3 lenses per relay, it requires as many as 27 lenses: this is not preferable for production costs, because of an increased parts count and much time taken for assembling.

SUMMARY OF THE INVENTION

Having been made in view of such problems with the prior art as mentioned above, the invention has for its object the provision of a relay optical system for rigid endoscopes that is fabricated at low costs by reducing a parts count while brightness is kept intact.

According to the invention, the aforesaid object is achievable by the provision of a rigid endoscope comprising a rigid endoscope optical system having an elongate insert and adapted to implement image transfer using a relay lens, wherein said relay lens comprises at least two rod lenses and satisfies the following condition:

$$Nd > 2 \quad (1)$$

where nd is the refractive index on d-line basis of each of said rod lenses in the said relay lens.

The rod lens here refers to an elongate rod-form lens whose axial thickness is at least five times as large as the outer diameter of the lens.

For the aforesaid relay lens, it is also preferable to satisfy the following conditions:

$$0.05 < \phi \cdot nd/L < 0.1 \quad (2)$$

$$30 < L/\phi < 40 \quad (3)$$

where $\phi$ stands for the outer diameter of the aforesaid relay lens, and L stands for the optical full length of the aforesaid relay lens.

It is also preferable to satisfy the following conditions with respect to the material used for the aforesaid rod lens:

$$\tau(350) \geq 75(\%) \quad (4)$$

$$\tau(320) \geq 30(\%) \quad (5)$$

where $\tau(350)$ represents the internal transmittance at a wavelength of 350 nm per 10 mm of the optical material used for the aforesaid rod lens, and $\tau(320)$ represents the internal transmittance at a wavelength of 320 nm per 10 mm of the optical material used for the aforesaid rod lens.

It is further preferable to satisfy the following conditions with respect to the material used for the aforesaid rod lens:

$$Nh < 1,000 \quad (6)$$

$$E > 900 \times 10^8 \text{ N/m}^2 \quad (7)$$

where N represents Knoop hardness, and E represents Young's modulus.

According to the relay optical system for rigid endoscopes of the invention, the number of relays is so reduced while making sure brightness that the parts count can be brought down, resulting in fabrication cost reductions. It is also possible to bring down the polishing cost for the rod lenses used for that relay optical system and make sure their resistance to breaking.

Still other objects and advantages of the invention will in part be obvious and will in part be apparent from the specification.

The invention accordingly comprises the features of construction, combinations of elements, arrangement of parts which will be exemplified in the construction hereinafter set forth, and the scope of the invention will be indicated in the claims.

BRIEF DESCRIPTION OF THE DRAWINGS

FIG. 4 is illustrative in section of an objective lens system (a) and an eyepiece lens system (b) in the rigid endoscope optical system of Example 1.

FIGS. 13(a) and 13(b) is are illustrative in section, as in FIG. 4, of the comparative example.

DESCRIPTION OF THE PREFERRED EMBODIMENTS

Figure 1:
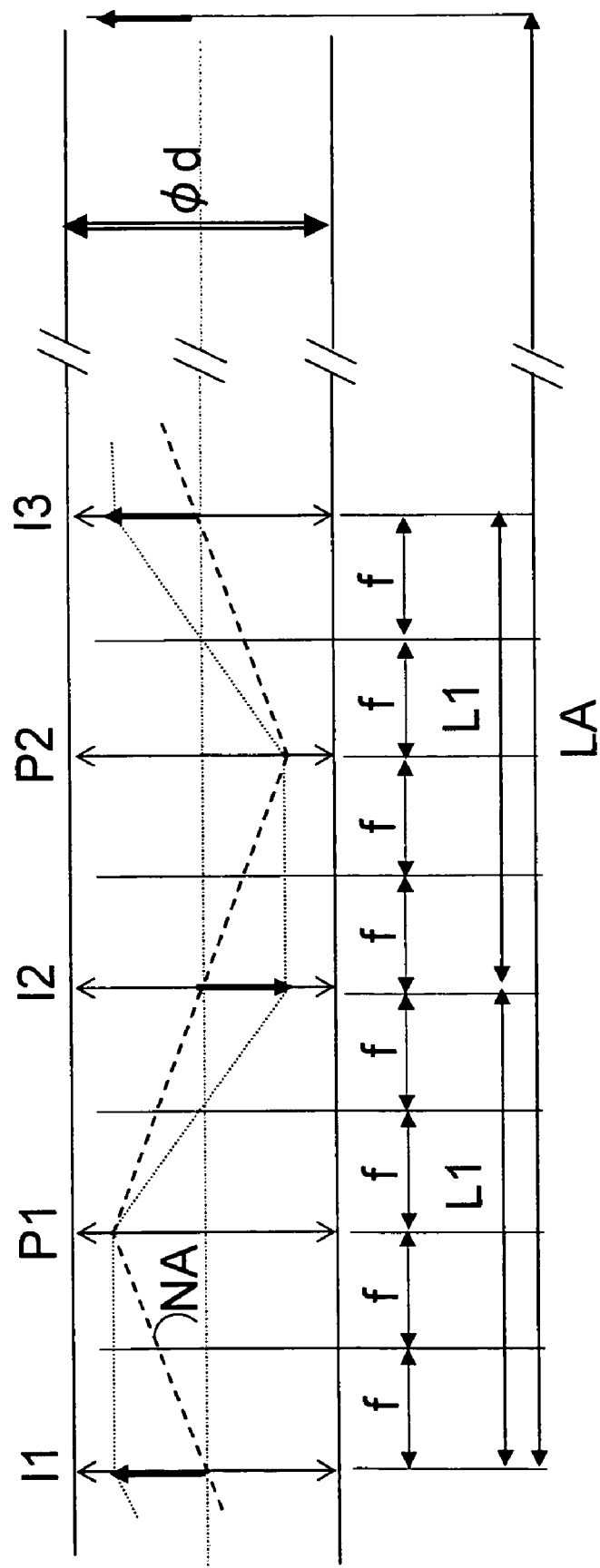
FIG. 1 is illustrative in schematic of the brightness of a relay lens in a rigid endoscope optical system.

The optical system for rigid endoscopes according to the invention is now explained.

Generally, the rigid endoscope optical system is designed such that an image formed through an objective lens is transferred through a relay optical system odd-number times to enlarge and view an erected image through an eyepiece optical system.

Although the brightness of the relay optical system may be enhanced almost in proportion of the square of the number of relays, yet this is not preferable because an increased parts count leads to increased costs.

Here suppose an optical system whose brightness is kept intact even with a decrease in the number of relays. The number of relays is an odd-number time: a possible way of reducing the number of relays is to reduce eleven down to nine, and nine down to seven.

Further, the brightness of the relay optical system is also known to build up almost in proportion of the square of the refractive index of the vitreous material for the rod lens constituting the relay optical system.

For the vitreous material applied to the rod lens, it is preferable to have a flat spectral transmittance in the visible range. This is to prevent even a relay optical system having an extended vitreous material path from being colored. Vitreous material F2 made by Schott AG is relatively less colored; so it is suitable for a rod lens. Note here that F2 has a refractive index of about 1.6.

These relations are summarized in Table 1 given below. For instance, when a nine relays type optical system using vitreous material F2 of Schott AG is brought down to a seven relays type, the refractive index of that rod lens required to keep brightness is going to be 2.064.

The number of 9 or more relays is not cost-preferable because of an increased parts count. As the number of relays increases, it gives rise to a lot more reflection losses due to air contact surfaces, ending up with decreasing light quantity. For these reasons, the number of relays for rigid endoscopes is preferably about seven.

In consideration of vitreous material having a refractive index larger than that of F2, therefore, the refractive index of the vitreous material required to keep brightness intact with a decrease in the number of relays should be 2 or more.

TABLE 1

| Number of Relays | (A) | (B) | (C) |
|---|---|---|---|
| 11→9 | 1.22 | 1.6 | 1.952 |
| 9→7 | 1.29 | 1.6 | 2.064 |
| 7→5 | 1.4 | 1.6 | 2.24 |

(A): Vitreous path (focal length) ratio before and after reductions in the number of relays;
(B): d-line refractive index of Schott F2; and
(C): Refractive index nd of the vitreous material required to keep brightness even with a reduced number of relays.

The brightness of the relay lens is now briefly explained with reference to the schematic view of FIG. 1.

Consider now a relay optical system of N relays. In FIG. 1, let I1, I2, I3 . . . stand for intermediate image planes having field lenses located on them, P1, P2 . . . stand for pupil planes having imaging lenses located on them, $\phi d$ stand for the outer diameter of the relay system, L1 stand for the relay length of one relay (the distance from one intermediate image plane to the next intermediate image plane: the optical full length of the relay lens), and LA stand for the whole relay length of N relays. Then, $$L1 = LA/N$$

The relay length of one relay, L1, is given by $$L1 = LA/N$$
$$= 4f$$

where f is the focal length of the imaging lenses located at P1, P2, . . . , and the field lenses located at I1, I2, I3 . . . .

Here, if the space between the image position I1 and the pupil position P1 is filled up with a vitreous material having a refractive index n, LA1 that is the length L1 as calculated on air basis is given by $$LA1 = L1/n \qquad (a)$$
$$= LA/Nn$$
$$= 4f'$$

Here consider NA in FIG. 1 as image brightness.

With the pupil diameter as almost the outer diameter of the relay system, NA is given by $$NA = (d/2)/2f'$$
$$= d/4f'$$

From equation (a), f'=LA/4Nn. Hence, $$NA = d \cdot Nn/LA$$

Since the brightness b of a certain image point is represented by the square of NA, $$b = NA_2$$
$$= (d \cdot Nn/LA)^2$$

Here consider the total light quantity B that can be transferred by the relay system. Since B is the product of the areas a and b, $$B = s \cdot b$$

From $$s = \pi \cdot (d/2)^2,$$
$$B = \pi \cdot (d/2)^2 \cdot (d \cdot Nn/LA)^2$$
$$= (\pi/4) \cdot d^4 \cdot N^2 \cdot n^2/LA^2$$

Using a constant C $(=(\pi/4)/LA^2)$ while the desired total relay length LA is thought of as being constant, one obtains $$B = C \cdot d^4 \cdot N^2 \cdot n^2 \qquad (b)$$

From this, the brightness of the whole system by the relay system would be proportional to the fourth power of the outer diameter of the relay system and the square of the number of relays and the refractive index, n, of the rod lens.

Therefore, the refractive index of the vitreous material must be changed from the original n1 to a new n2 so as to reduce the number of relays from N1 down to N2 (N1>N2) and keep brightness constant. From equation (b), that ratio $$n2=N1/N2\cdot n1$$

Thus, one obtains the relations set out in Table 1.

Condition (1) here stands for the refractive index on d-line basis of the material used for the rod lens. As the lower limit of 2 is not reached, it is impossible to keep brightness at the desired insert length.

Condition (2) is about the brightness of the relay optical system. As the lower limit of 0.05 is not reached, the relay optical system runs short of brightness, and as the upper limit of 0.1 is exceeded, it causes the refractive index of the rod lens to grow unacceptably too high.

Condition (3) is about the length and outer diameter of the rod lens. As the lower limit of 30 is not reached, the rod lens runs short of brightness, and as the upper limit of 40 is exceeded, the lens grows too long relative to diameter, which is not preferable in terms of resistance to breaking.

Conditions (4) and (5) are about the spectral transmittance of the rod lens. A rigid endoscope for the urinary organs that has a few relays has a vitreous path length of as long as about 200 mm; so coloring after passing through the glass has influences on color reproducibility. For the glass it is desired to have high transmittance per unit length so as to be less colored even with a long vitreous path. At below the lower limit of 75% to transmittance (4), the rod lens runs short of brightness, and at below the lower limit to 30% to condition (5), there is the transmittance for blue color going down; when such glass is used for the rod lens having an extended vitreous path, it is seen in yellowish color. In other words, it is not preferable for use on endoscopes.

Condition (6) is about the Knoop hardness of uni-axial single crystals. A glass exceeding the upper limit of 1,000 is not preferable because its ability to be polished goes worse: it is difficult to process and costs much. The Knoop hardness of generally available sapphire is on the order of 1,400, on which it is very difficult, if not possible, to polish it in convex form: polishing sapphire is not that preferable because it is time consuming and costs much. Although generally available optical glass has a Knoop hardness of about 700 at most, yet the material used here has a Knoop hardness of preferably 1,000 or lower, more preferably 800 or lower, so as to facilitate polishing it in convex form.

Condition (7) is about the Young's modulus of uni-axial single crystals. A glass falling short of the lower limit of $900\times10^8$ N/m² is not preferable because its resistance to breaking goes down. Ordinary optical glass has a Young's modulus of about $700\times10^8$ N/m², at which a rod lens fabricated from it is often going to break, crack or fail.

As noted above, reducing the number of relays without changing the total relay length is nothing more than extending the whole length of the rod lens. This works more against the resistance to breaking, and to overcome this, the resistance to breaking must be greater than that of ordinary glass. In other words, it is preferable to have a Young's modulus of at least $900\times10^8$ N/m².

Among what has been considered here as materials having high refractive indices, there are KT Crystal (nd≈2.24) made by NTT Advanced Technology Co. Ltd., an optical material (nd≈2.18) set forth in International Patent WO2005/049897, rutile ($TiO_2$, $n_o$=2.61, $n_e$=2.9), and diamond (nd≈2.42).

The rigid endoscope optical system of the invention is now explained with reference to inventive and comparative examples.

Figure 2:
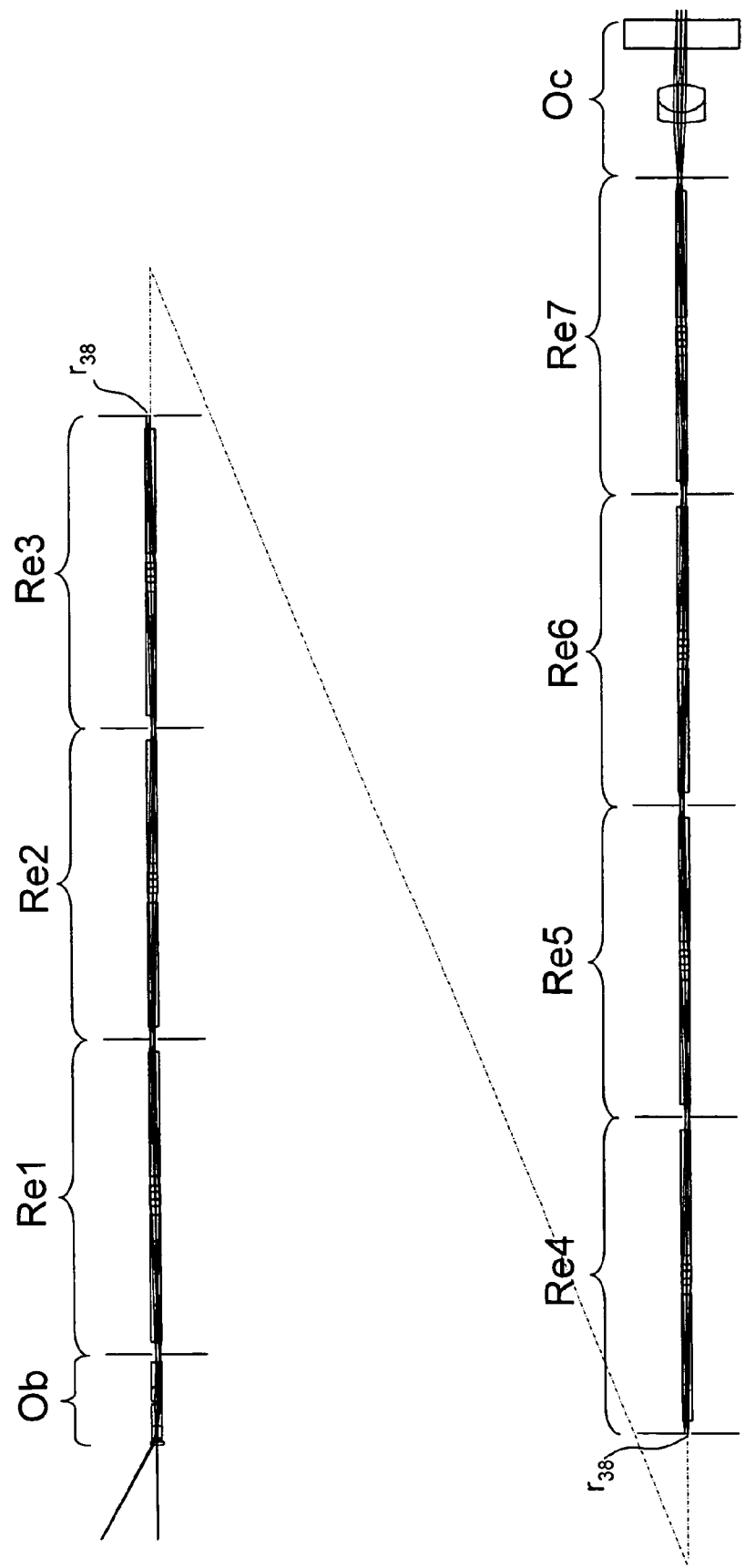
FIG. 2 is illustrative in section of the rigid endoscope optical system of Example 1 according to the invention, as viewed through the optical axis of the whole thereof.
Figure 3:
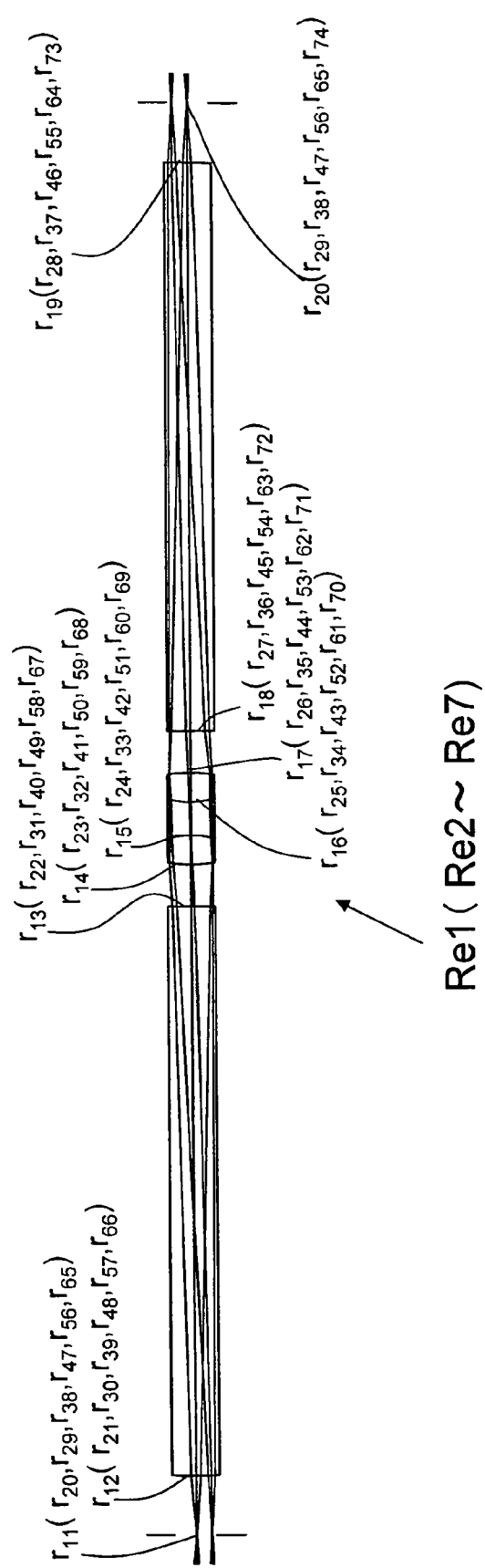
FIG. 3 is a sectional view of one exemplary relay lens system that constitutes part of the rigid endoscope optical system of Example 1.

A sectional view, as viewed through an optical axis, of the whole of the rigid endoscope optical system of Example 1 is shown in FIG. 2 (note here that the whole optical system is too long along the linear optical axis: the optical axis is parted into two on the way, and an optical axis portion between them is indicated by a one-dotted chain line of Z shape to show the whole arrangement); a sectional view of one of relay lens systems (relay lenses, relay optical systems) constituting that rigid endoscope optical system is shown in FIG. 3; and an objective lens system (a) and an eyepiece lens system (b) in that rigid endoscope optical system are shown in FIG. 4.

About the optical system here, there will be numerical data given later, wherein the surface number for an optical surface as counted from the side of the objective lens system is indicated by "No.", the radius of curvature by "r", a surface-to-surface spacing or an air spacing by "d", a d-line refractive index by "nd", and an Abbe constant by "vd". The radius of curvature and the surface-to-surface spacing are given in mm. Throughout FIGS. 2 to 4 as well as other inventive examples and a comparative example, optical surfaces (some of which are virtual surfaces) having surface Nos. 1, 2, 3, . . . are indicated by $r_1, r_2, r_3, \ldots$.

As shown in FIG. 2, the rigid endoscope optical system of Example 1 comprises seven relay lens systems Re1 to Re7 which are of the same construction and arranged coaxially, an objective lens system Ob located coaxially at a frontal end, and an eyepiece lens system Oc located coaxially at a distal end. As shown in FIG. 3, the relay lens systems Re1 to Re7 are each made up of a rod lens defined by a convex-plano positive lens and a rod lens defined by a plano-convex positive lens, and there is a triplet positive lens located between them, which is composed of three lenses: a double-convex positive lens, a double-concave negative lens and a double-convex positive lens. More specifically, both rod lenses of the same shape are located symmetrically with respect to plane such that they are opposite to each other on their plane sides, and the triplet positive lens of shape symmetrical with respect to plane is located between those planes. In each of the relay lens systems Re1 to Re7, a double-concave positive air lens defined between the convex surfaces of the adjacent rod lenses works as a field lens, and the middle triplet positive lens works as an imaging lens.

The objective lens system Ob is made up of, in order from its object side, a cover glass, a plano-concave negative lens, a plano-convex positive lens and a cemented lens of a double-convex positive lens and a negative meniscus lens convex on its image side, as shown in FIG. 4(a), and the eyepiece lens system Oc is made up of a cemented lens of a negative meniscus lens convex on its object side and a double-convex positive lens, and a cover glass, as shown in FIG. 4(b).

In the numerical data given later, surface No. 6 refers to a stop surface that is a virtual surface, and it is actually the aperture of the triplet positive lens in each of the relay lens systems Re1 to Re7 that takes a stop role in stopping down light beams. Surface Nos. 11, 20, 29, 38, 47, 56, 65 and 74 are each an intermediate image plane that is again a virtual surface, and of them, the intermediate image plane of surface No. 11 is an image plane defined by the objective lens system Ob, and surface No. 74 is an image plane defined by the relay lens system Re7, providing an object plane of the eyepiece lens system Oc. Surface Nos. 20, 29, 38, 47, 56 and 65 are each an intermediate image plane formed between the respective relay lens systems Re1 to Re7. Surface No. 80 is indicative of the position of an eye point (exit pupil) of the optical system here.

With such arrangement as described above, astigmatism and axial chromatic aberration are well corrected.

In the example here, the relay lens systems Re1 to Re7 are each formed of the vitreous material set forth in Patent Publication 1; condition (1) with respect to nd is 2.177; the relay lens systems Re1 to Re7 each have an outer diameter φ of 1.1 mm; the relay lens systems Re1 to Re7 have an optical total length L of 33.87 mm; condition (2) with respect to φ·nd/L is 0.071; condition (3) with respect to L/φ is 30.79; an F-number (brightness) is 7.31; an optical total length (objective lens system-eyepiece lens system) is 246.7 mm; the number of relays is 7; and the number of relay lens units is 21.

Figure 5:
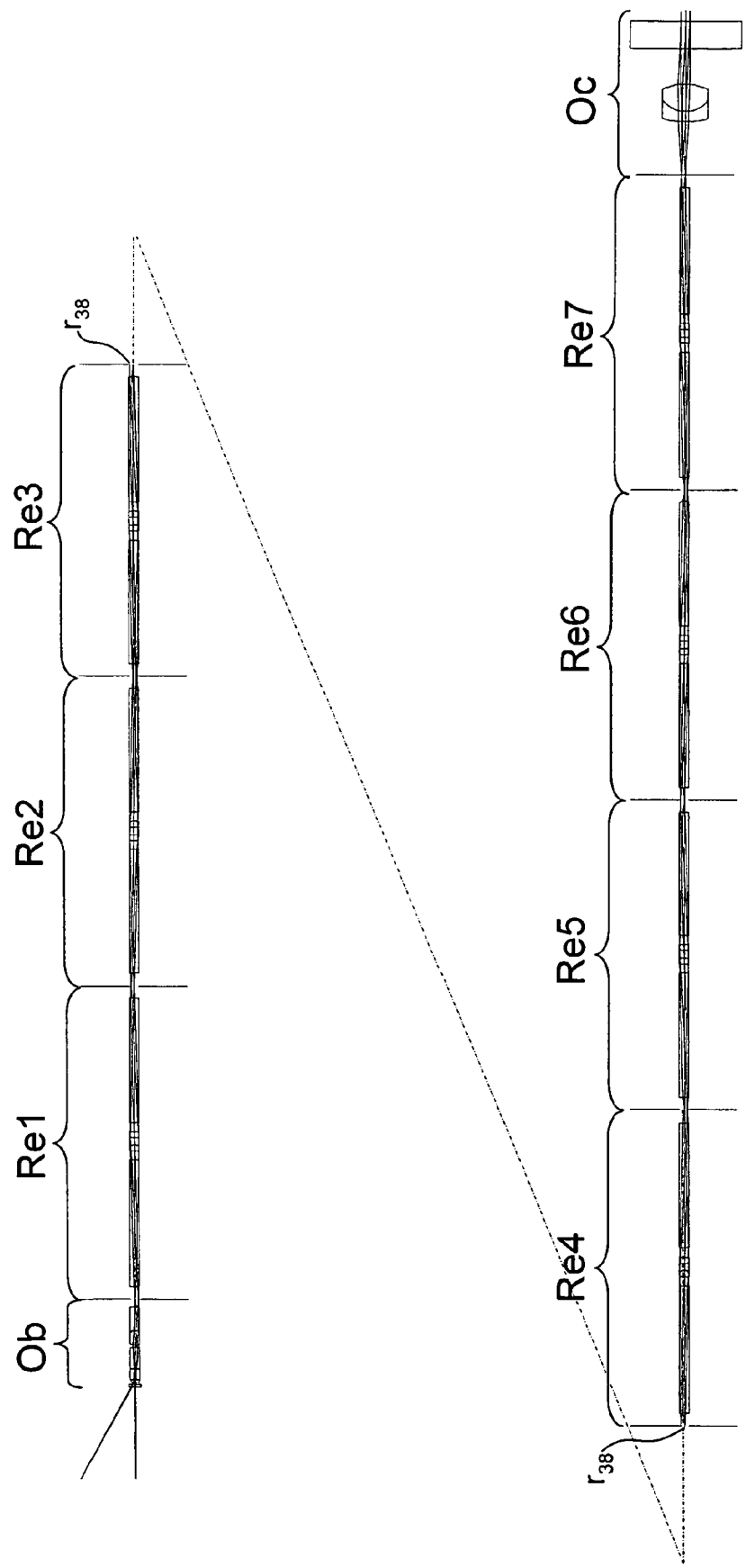
FIG. 5 is illustrative in section of the rigid endoscope optical system of Example 2 according to the invention, as viewed through the optical axis of the whole thereof.
Figure 6:
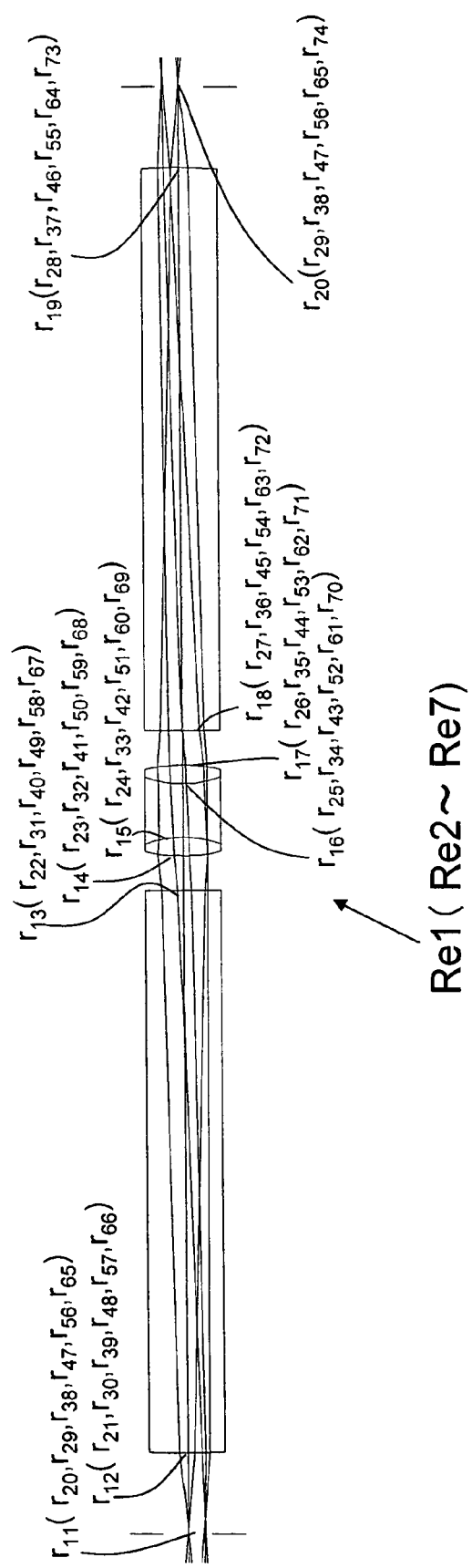
FIG. 6 is a sectional view of one exemplary relay lens system that constitutes part of the rigid endoscope optical system of Example 2.

A sectional view, as in FIG. 2, of Example 2 as viewed through the optical axis of the whole in shown in FIG. 5; a sectional view, as in FIG. 3, of the relay lens system according to Example 2 is shown in FIG. 6; and a sectional view, as in FIG. 4, of an objective lens system and an eyepiece lens system is shown in FIG. 7.

Example 2 is much the same in construction as Example 1, and the relay lens systems Re1 to Re7 each have rod lenses fabricated from KT Crystal made by NTT Advanced Technology Co., Ltd.

That is, as shown in FIG. 5, the rigid endoscope optical system of Example 2 comprises seven relay lens systems Re1 to Re7 which are of the same construction and arranged coaxially, an objective lens system Ob located coaxially at a frontal end, and an eyepiece lens system Oc located coaxially at a distal end. As shown in FIG. 6, the relay lens systems Re1 to Re7 are each made up of a rod lens defined by a convex-plano positive lens and a rod lens defined by a plano-convex positive lens, and there is a triplet positive lens located between them, which is composed of three lenses: a double-convex positive lens, a double-concave negative lens and a double-convex positive lens. More specifically, both rod lenses of the same shape are located symmetrically with respect to plane such that they are opposite to each other on their plane sides, and the triplet positive lens of shape symmetrical with respect to plane is located between those planes. In each of the relay lens systems Re1 to Re7, a double-concave positive air lens defined between the convex surfaces of the adjacent rod lenses works as a field lens, and the middle triplet positive lens works as an imaging lens.

Figure 7A:
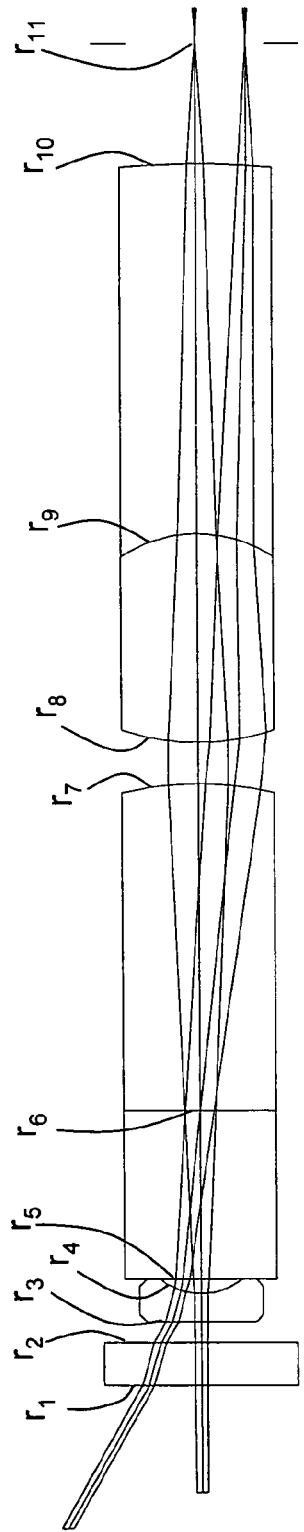
FIG. 7 is illustrative in section of an objective lens system (a) and an eyepiece lens system (b) in the rigid endoscope optical system of Example 2.
Figure 7B:
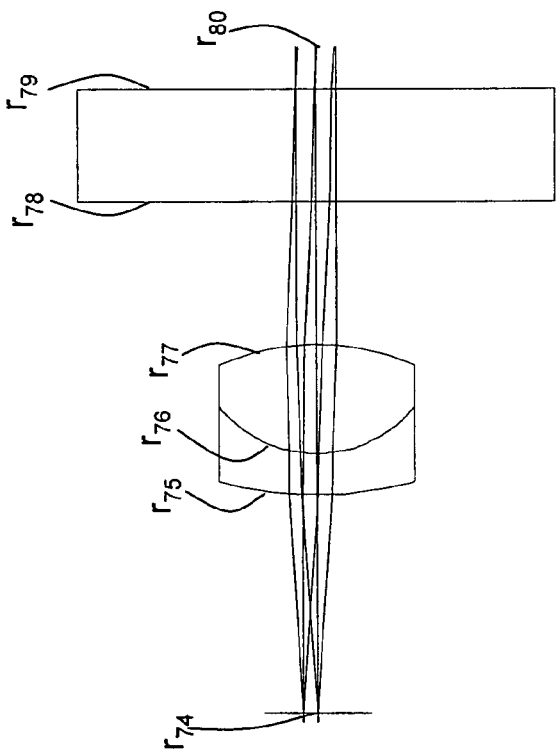

The objective lens system Ob is made up of, in order from its object side, a cover glass, a plano-concave negative lens, a plano-convex positive lens and a cemented lens of a double-convex positive lens and a negative meniscus lens convex on its image side, as shown in FIG. 7(a), and the eyepiece lens system Oc is made up of a cemented lens of a negative meniscus lens convex on its object side and a double-convex positive lens, and a cover glass, as shown in FIG. 7(b).

In the numerical data given later, surface No. 6 refers to a stop surface that is a virtual surface, and it is actually the aperture of the triplet positive lens in each of the relay lens systems Re1 to Re7 that takes a stop role in stopping down light beams. Surface Nos. 11, 20, 29, 38, 47, 56, 65 and 74 are each an intermediate image plane that is again a virtual surface, and of them, the intermediate image plane of surface No. 11 is an image plane defined by the objective lens system Ob, and surface No. 74 is an image plane defined by the relay lens system Re7, providing an object plane of the eyepiece lens system Oc. Surface Nos. 20, 29, 38, 47, 56 and 65 are each an intermediate image plane formed between the respective relay lens systems Re1 to Re7. Surface No. 80 is indicative of the position of an eye point (exit pupil) of the optical system here.

With such arrangement as described above, astigmatism and axial chromatic aberration are well corrected.

In the example here, condition (1) with respect to nd is 2.24; the relay lens systems Re1 to Re7 each have an outer diameter φ of 1.1 mm; the relay lens systems Re1 to Re7 have an optical total length L of 34.66 mm; condition (2) with respect to φ·nd/L is 0.071; condition (3) with respect to L/φ is 31.51; an F-number (brightness) is 7.33; an optical total length (objective lens system-eyepiece lens system) is 252.2 mm; the number of relays is 7; and the number of relay lens units is 21.

Figure 8:
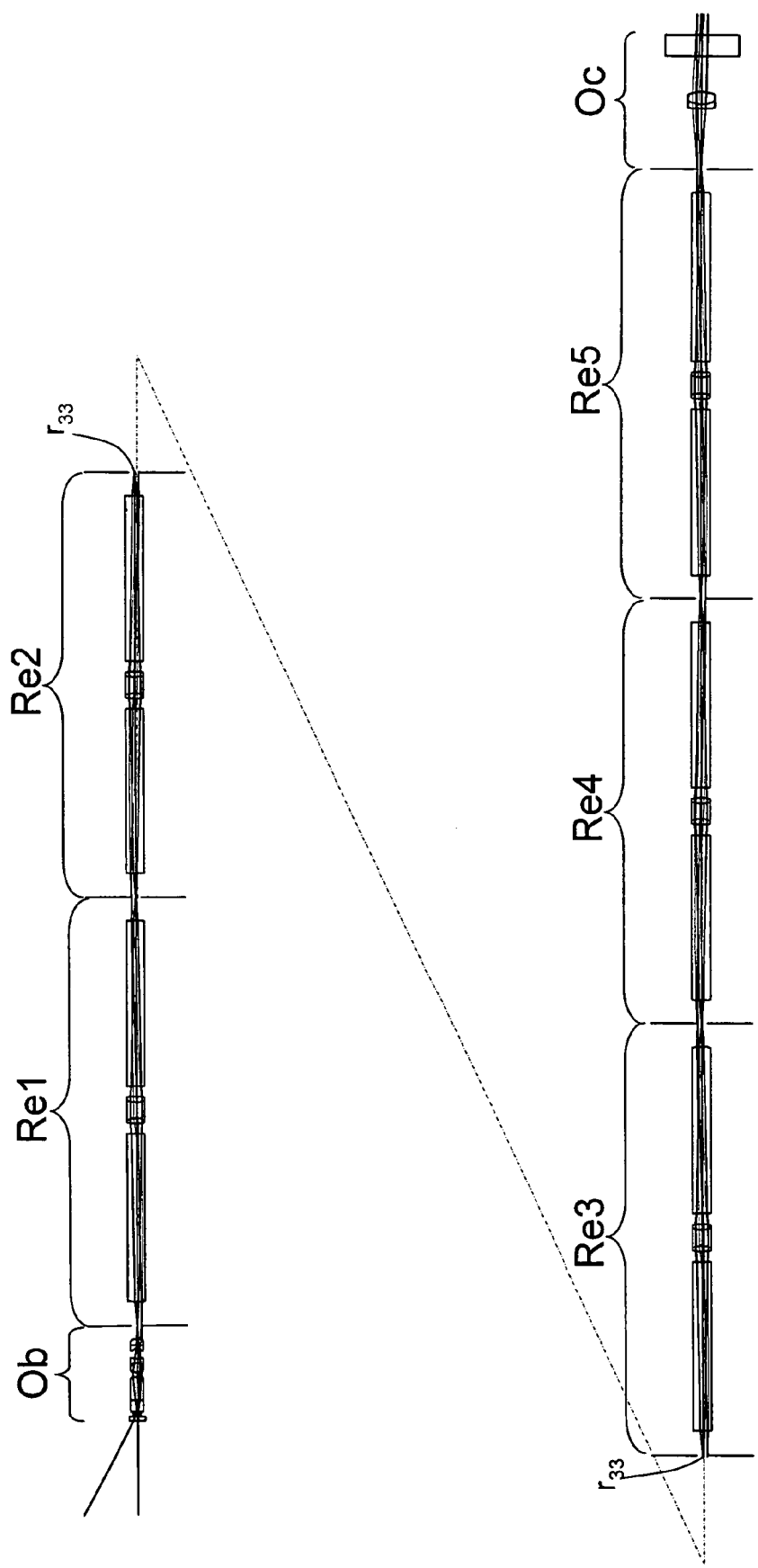
FIG. 8 is illustrative in section of the rigid endoscope optical system of Example 3 according to the invention, as viewed through the optical axis of the whole thereof.
Figure 9:
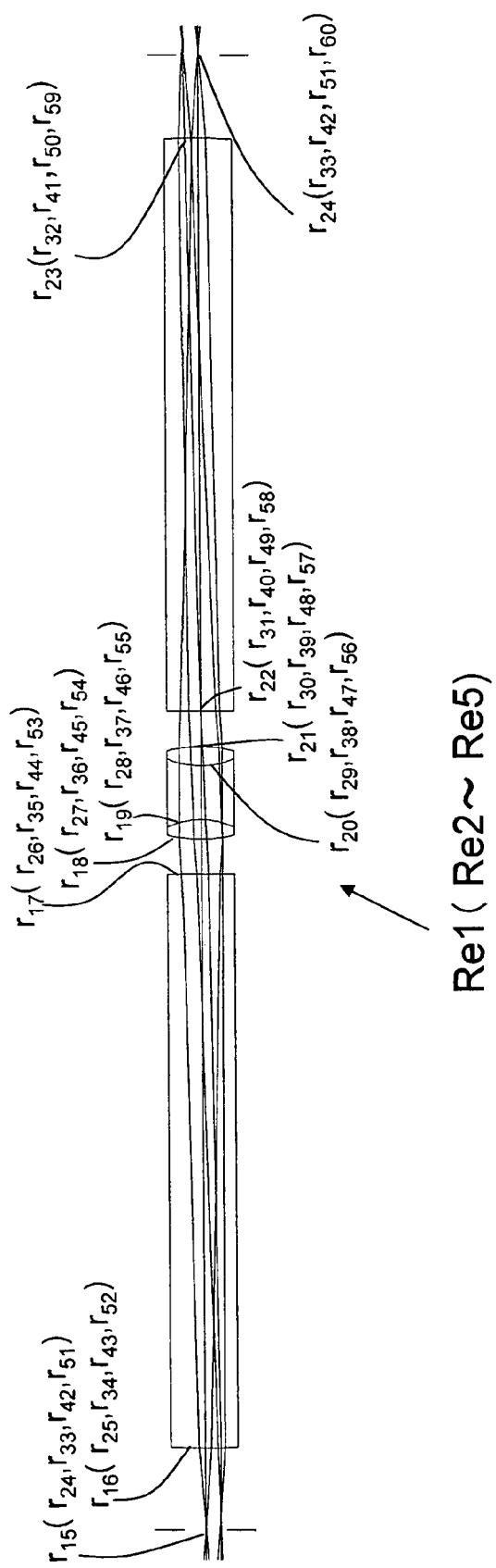
FIG. 9 is a sectional view of one exemplary relay lens system that constitutes part of the rigid endoscope optical system of Example 3.

A sectional view, as in FIG. 2, of Example 3 as viewed through the optical axis of the whole is shown in FIG. 8; a sectional view, as in FIG. 3, of the relay lens system according to Example 3 is shown in FIG. 9; and a sectional view, as in FIG. 4, of an objective lens system and an eyepiece lens system is shown in FIG. 10.

As shown in FIG. 8, the rigid endoscope optical system of Example 3 comprises five relay lens systems Re1 to Re5 which are of the same construction and arranged coaxially, an objective lens system Ob located coaxially at a frontal end, and an eyepiece lens system Oc located coaxially at a distal end. As shown in FIG. 9, the relay lens systems Re1 to Re5 are each made up of a rod lens defined by a convex-plano positive lens and a rod lens defined by a plano-convex positive lens, and there is a triplet positive lens located between them, which is composed of three lenses: a double-convex positive lens, a double-concave negative lens and a double-convex positive lens. More specifically, both rod lenses of the same shape are located symmetrically with respect to plane such that they are opposite to each other on their plane sides, and the triplet positive lens of shape symmetrical with respect to plane is located between those planes. In each of the relay lens systems Re1 to Re5, a double-concave positive air lens defined between the convex surfaces of the adjacent rod lenses works as a field lens, and the middle triplet positive lens works as an imaging lens.

Figure 10A:
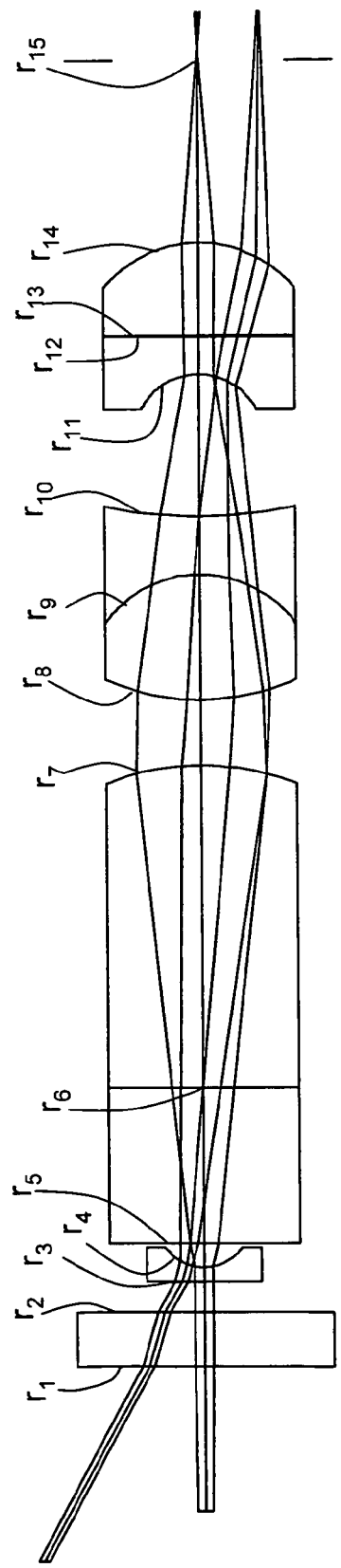
FIG. 10 is illustrative in section of an objective lens system (a) and an eyepiece lens system (b) in the rigid endoscope optical system of Example 3.
Figure 10B:
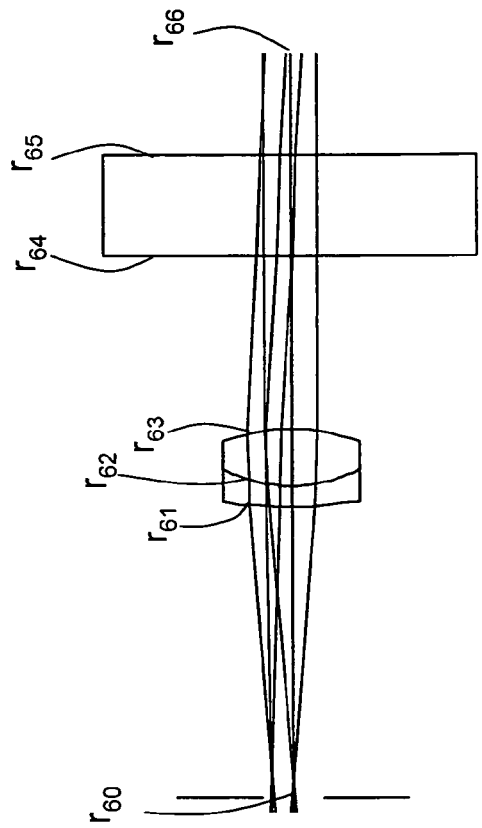

The objective lens system Ob is made up of, in order from its object side, a cover glass, a plano-concave negative lens, a plano-convex positive lens, a cemented lens of a double-convex positive lens and a double-concave negative lens and a cemented lens of a concavo-plano negative lens and a plano-convex positive lens, as shown in FIG. 10(a), and the eyepiece lens system Oc is made up of a cemented lens of a negative meniscus lens convex on its object side and a double-convex positive lens, and a cover glass, as shown in FIG. 10(b).

In the numerical data given later, surface No. 6 refers to a stop surface that is a virtual surface, and it is actually the aperture of the triplet positive lens in each of the relay lens systems Re1 to Re5 that takes a stop role in stopping down light beams. Surface Nos. 15, 24, 33, 42, 51 and 60 are each an intermediate image plane that is again a virtual surface, and of them, the intermediate image plane of surface No. 15 is an image plane defined by the objective lens system Ob, and surface No. 60 is an image plane defined by the relay lens system Re5, providing an object plane of the eyepiece lens system Oc. Surface Nos. 24, 33, 42 and 51 are each an intermediate image plane formed between the respective relay lens systems Re1 to Re5. Surface No. 66 is indicative of the position of an eye point (exit pupil) of the optical system here.

With such arrangement as described above, astigmatism and axial chromatic aberration are well corrected.

In the example here, the relay lens systems Re1 to Re5 each have rod lenses fabricated from synthesized rutile; condition (1) with respect to nd is 2.62; the relay lens systems Re1 to Re5 each have an outer diameter φ of 1.7 mm; the relay lens systems Re1 to Re5 have an optical total length L of 63.01 mm; condition (2) with respect to φ·nd/L is 0.071; condition (3) with respect to L/φ is 37.06; an F-number (brightness) is 6.34; an optical total length (objective lens system-eyepiece lens system) is 328.8 mm; the number of relays is 5; and the number of relay lens units is 15.

A comparative example with inventive Examples 1 to 3 is now explained. A sectional view, as in FIG. 2, of the comparative example as viewed through the optical axis of the whole is shown in FIG. 11; a sectional view, as in FIG. 3, of the relay lens system according to the comparative example is shown in FIG. 12; and a sectional view, as in FIG. 4, of an objective lens system and an eyepiece lens system is shown in FIG. 13.

Figure 11:
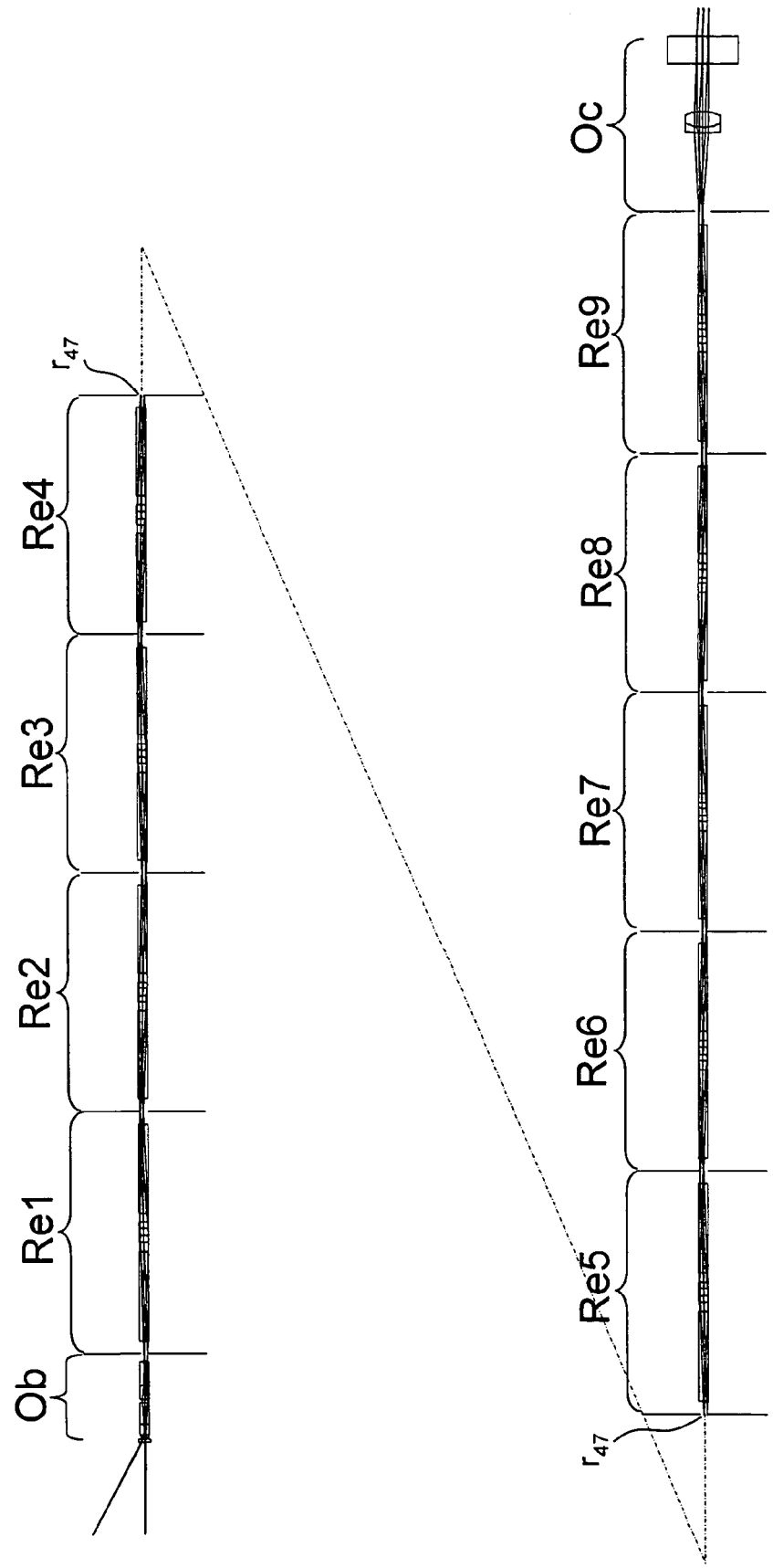
FIG. 11 is illustrative in section, as in FIG. 2, of a comparative example for the invention.
Figure 12:
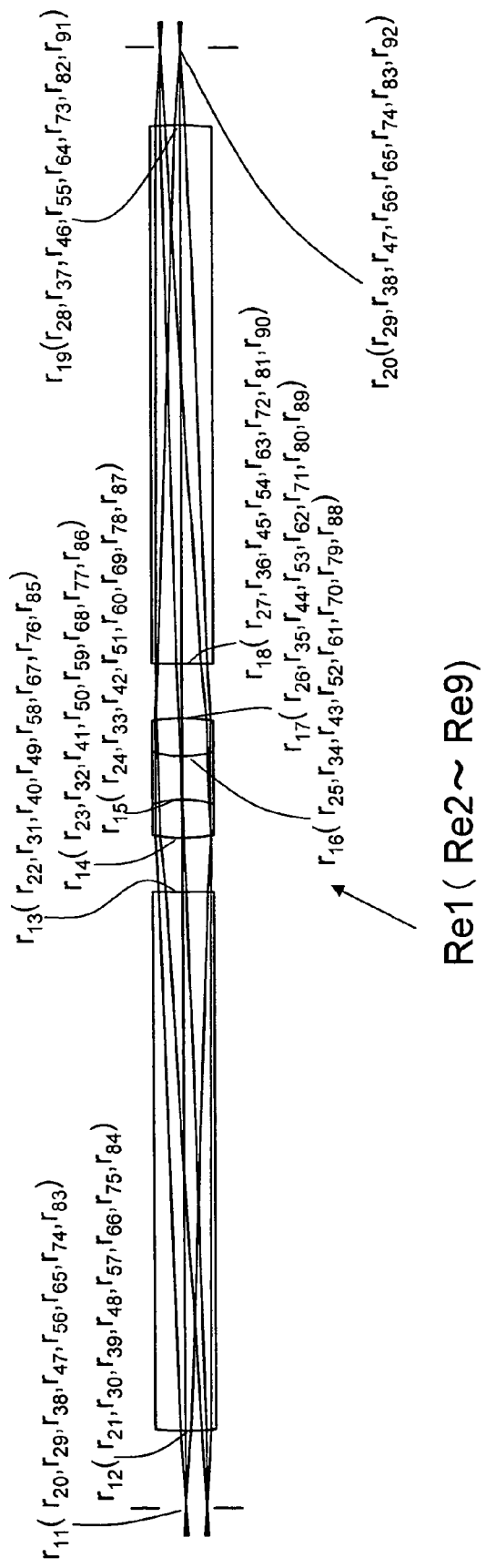
FIG. 12 is illustrative in section, as in FIG. 3, of the comparative example.

As shown in FIG. 11, the rigid endoscope optical system of this comparative example comprises nine relay lens systems Re1 to Re9 which are of the same construction and arranged coaxially, an objective lens system Ob located coaxially at a frontal end, and an eyepiece lens system Oc located coaxially at a distal end. As shown in FIG. 12, the relay lens systems Re1 to Re9 are each made up of a rod lens defined by a convex-plano positive lens and a rod lens-defined by a plano-convex positive lens, and there is a triplet positive lens located between them, which is composed of three lenses: a double-convex positive lens, a double-concave negative lens and a double-convex positive lens. More specifically, both rod lenses of the same shape are located symmetrically with respect to plane such that they are opposite to each other on their plane sides, and the triplet positive lens of shape symmetrical with respect to plane is located between those planes. In each of the relay lens systems Re1 to Re9, a double-concave positive air lens defined between the convex surfaces of the adjacent rod lenses works as a field lens, and the middle triplet positive lens works as an imaging lens.

Explanation of the objective lens system Ob of FIG. 13(*a*) and the eyepiece lens system Oc of FIG. 13(*b*) are left out, because of being the same as in Example 1 of FIG. 4.

In the numerical data given later, surface No. 6 refers to a stop surface that is a virtual surface, and it is actually the aperture of the triplet positive lens in each of the relay lens systems Re1 to Re9 that takes a stop role in stopping down light beams. Surface Nos. 11, 20, 29, 38, 47, 56, 65, 74, 83 and 92 are each an intermediate image plane that is again a virtual surface, and of them, the intermediate image plane of surface No. 11 is an image plane defined by the objective lens system Ob, and surface No. 92 is an image plane defined by the relay lens system Re9, providing an object plane of the eyepiece lens system Oc. Surface Nos. 20, 29, 38, 47, 56, 65, 74 and 83 are each an intermediate image plane formed between the respective relay lens systems Re1 to Re9.

In the comparative example here, condition (1) with respect to nd is 1.59; the relay lens systems Re1 to Re9 each have an outer diameter φ of 1.1 mm; the relay lens systems Re1 to Re9 have an optical total length L of 26.53 mm; condition (2) with respect to φ·nd/L is 0.066; condition (3) with respect to L/φ is 24.12; an F-number (brightness) is 7.32; an optical total length (objective lens system-eyepiece lens system) is 248.3 mm; the number of relays is 9; and the number of relay lens units is 27.

Set out below are numerical data about Examples 1 to 3 as well as the single comparative example.

EXAMPLE 1

| No | r | d | nd | vd |
|---|---|---|---|---|
| 1 | ∞ | 0.300 | 1.76820 | 64.10 |
| 2 | ∞ | 0.150 | | |
| 3 | ∞ | 0.200 | 1.88300 | 40.76 |
| 4 | 0.492 | 0.100 | | |
| 5 | ∞ | 1.200 | 2.00330 | 28.27 |
| 6 | ∞ | 2.350 | 2.00330 | 28.27 |
| 7 | −2.366 | 0.300 | | |
| 8 | 1.739 | 1.500 | 1.70000 | 48.08 |
| 9 | −1.020 | 2.640 | 1.92286 | 18.90 |
| 10 | −5.875 | 0.850 | | |
| 11 | ∞ | 1.380 | | |
| 12 | 9.384 | 13.457 | 2.17700 | 23.50 |
| 13 | ∞ | 1.000 | | |
| 14 | 3.300 | 0.700 | 1.62230 | 53.17 |
| 15 | −1.922 | 0.800 | 1.77250 | 49.60 |
| 16 | 1.922 | 0.700 | 1.62230 | 53.17 |
| 17 | −3.300 | 1.000 | | |
| 18 | ∞ | 13.457 | 2.17700 | 23.50 |
| 19 | −9.384 | 1.380 | | |
| 20 | ∞ | 1.380 | | |
| 21 | 9.384 | 13.457 | 2.17700 | 23.50 |
| 22 | ∞ | 1.000 | | |
| 23 | 3.300 | 0.700 | 1.62230 | 53.17 |
| 24 | −1.922 | 0.800 | 1.77250 | 49.60 |
| 25 | 1.922 | 0.700 | 1.62230 | 53.17 |
| 26 | −3.300 | 1.000 | | |
| 27 | ∞ | 13.457 | 2.17700 | 23.50 |
| 28 | −9.384 | 1.380 | | |
| 29 | ∞ | 1.380 | | |
| 30 | 9.384 | 13.457 | 2.17700 | 23.50 |
| 31 | ∞ | 1.000 | | |
| 32 | 3.300 | 0.700 | 1.62230 | 53.17 |
| 33 | −1.922 | 0.800 | 1.77250 | 49.60 |
| 34 | 1.922 | 0.700 | 1.62230 | 53.17 |
| 35 | −3.300 | 1.000 | | |
| 36 | ∞ | 13.457 | 2.17700 | 23.50 |
| 37 | −9.384 | 1.380 | | |
| 38 | ∞ | 1.380 | | |
| 39 | 9.384 | 13.457 | 2.17700 | 23.50 |
| 40 | ∞ | 1.000 | | |
| 41 | 3.300 | 0.700 | 1.62230 | 53.17 |
| 42 | −1.922 | 0.800 | 1.77250 | 49.60 |
| 43 | 1.922 | 0.700 | 1.62230 | 53.17 |
| 44 | −3.300 | 1.000 | | |
| 45 | ∞ | 13.457 | 2.17700 | 23.50 |
| 46 | −9.384 | 1.380 | | |
| 47 | ∞ | 1.380 | | |
| 48 | 9.384 | 13.457 | 2.17700 | 23.50 |
| 49 | ∞ | 1.000 | | |
| 50 | 3.300 | 0.700 | 1.62230 | 53.17 |
| 51 | −1.922 | 0.800 | 1.77250 | 49.60 |
| 52 | 1.922 | 0.700 | 1.62230 | 53.17 |
| 53 | −3.300 | 1.000 | | |
| 54 | ∞ | 13.457 | 2.17700 | 23.50 |
| 55 | −9.384 | 1.380 | | |
| 56 | ∞ | 1.380 | | |
| 57 | 9.384 | 13.457 | 2.17700 | 23.50 |
| 58 | ∞ | 1.000 | | |
| 59 | 3.300 | 0.700 | 1.62230 | 53.17 |
| 60 | −1.922 | 0.800 | 1.77250 | 49.60 |
| 61 | 1.922 | 0.700 | 1.62230 | 53.17 |
| 62 | −3.300 | 1.000 | | |
| 63 | ∞ | 13.457 | 2.17700 | 23.50 |
| 64 | −9.384 | 1.380 | | |
| 65 | ∞ | 1.380 | | |
| 66 | 9.384 | 13.457 | 2.17700 | 23.50 |
| 67 | ∞ | 1.000 | | |
| 68 | 3.300 | 0.700 | 1.62230 | 53.17 |
| 69 | −1.922 | 0.800 | 1.77250 | 49.60 |
| 70 | 1.922 | 0.700 | 1.62230 | 53.17 |

-continued

| No | r | d | nd | vd |
|---|---|---|---|---|
| 71 | −3.300 | 1.000 | | |
| 72 | ∞ | 13.457 | 2.17700 | 23.50 |
| 73 | −9.384 | 1.380 | | |
| 74 | ∞ | 5.825 | | |
| 75 | 9.745 | 1.110 | 1.84666 | 23.78 |
| 76 | 3.281 | 2.930 | 1.67003 | 47.23 |
| 77 | −6.202 | 3.820 | | |
| 78 | ∞ | 3.000 | 1.76819 | 71.79 |
| 79 | ∞ | 1.150 | | |
| 80 | ∞ | | | |

EXAMPLE 2

| No | r | d | nd | vd |
|---|---|---|---|---|
| 1 | ∞ | 0.300 | 1.76820 | 64.10 |
| 2 | ∞ | 0.150 | | |
| 3 | ∞ | 0.200 | 1.88300 | 40.76 |
| 4 | 0.492 | 0.100 | | |
| 5 | ∞ | 1.200 | 2.00330 | 28.27 |
| 6 | ∞ | 2.350 | 2.00330 | 28.27 |
| 7 | −2.366 | 0.300 | | |
| 8 | 1.739 | 1.500 | 1.70000 | 48.08 |
| 9 | −1.020 | 2.640 | 1.92286 | 18.90 |
| 10 | −5.875 | 0.850 | | |
| 11 | ∞ | 1.380 | | |
| 12 | 9.886 | 13.848 | 2.24000 | 23.50 |
| 13 | ∞ | 1.000 | | |
| 14 | 3.300 | 0.700 | 1.62230 | 53.17 |
| 15 | −1.922 | 0.800 | 1.77250 | 49.60 |
| 16 | 1.922 | 0.700 | 1.62230 | 53.17 |
| 17 | −3.300 | 1.000 | | |
| 18 | ∞ | 13.848 | 2.24000 | 23.50 |
| 19 | −9.886 | 1.380 | | |
| 20 | ∞ | 1.380 | | |
| 21 | 9.886 | 13.848 | 2.24000 | 23.50 |
| 22 | ∞ | 1.000 | | |
| 23 | 3.300 | 0.700 | 1.62230 | 53.17 |
| 24 | −1.922 | 0.800 | 1.77250 | 49.60 |
| 25 | 1.922 | 0.700 | 1.62230 | 53.17 |
| 26 | −3.300 | 1.000 | | |
| 27 | ∞ | 13.848 | 2.24000 | 23.50 |
| 28 | −9.886 | 1.380 | | |
| 29 | ∞ | 1.380 | | |
| 30 | 9.886 | 13.848 | 2.24000 | 23.50 |
| 31 | ∞ | 1.000 | | |
| 32 | 3.300 | 0.700 | 1.62230 | 53.17 |
| 33 | −1.922 | 0.800 | 1.77250 | 49.60 |
| 34 | 1.922 | 0.700 | 1.62230 | 53.17 |
| 35 | −3.300 | 1.000 | | |
| 36 | ∞ | 13.848 | 2.24000 | 23.50 |
| 37 | −9.886 | 1.380 | | |
| 38 | ∞ | 1.380 | | |
| 39 | 9.886 | 13.848 | 2.24000 | 23.50 |
| 40 | ∞ | 1.000 | | |
| 41 | 3.300 | 0.700 | 1.62230 | 53.17 |
| 42 | −1.922 | 0.800 | 1.77250 | 49.60 |
| 43 | 1.922 | 0.700 | 1.62230 | 53.17 |
| 44 | −3.300 | 1.000 | | |
| 45 | ∞ | 13.848 | 2.24000 | 23.50 |
| 46 | −9.886 | 1.380 | | |
| 47 | ∞ | 1.380 | | |
| 48 | 9.886 | 13.848 | 2.24000 | 23.50 |
| 49 | ∞ | 1.000 | | |
| 50 | 3.300 | 0.700 | 1.62230 | 53.17 |
| 51 | −1.922 | 0.800 | 1.77250 | 49.60 |
| 52 | 1.922 | 0.700 | 1.62230 | 53.17 |
| 53 | −3.300 | 1.000 | | |
| 54 | ∞ | 13.848 | 2.24000 | 23.50 |
| 55 | −9.886 | 1.380 | | |
| 56 | ∞ | 1.380 | | |

-continued

| No | r | d | nd | vd |
|---|---|---|---|---|
| 57 | 9.886 | 13.848 | 2.24000 | 23.50 |
| 58 | ∞ | 1.000 | | |
| 59 | 3.300 | 0.700 | 1.62230 | 53.17 |
| 60 | −1.922 | 0.800 | 1.77250 | 49.60 |
| 61 | 1.922 | 0.700 | 1.62230 | 53.17 |
| 62 | −3.300 | 1.000 | | |
| 63 | ∞ | 13.848 | 2.24000 | 23.50 |
| 64 | −9.886 | 1.380 | | |
| 65 | ∞ | 1.380 | | |
| 66 | 9.886 | 13.848 | 2.24000 | 23.50 |
| 67 | ∞ | 1.000 | | |
| 68 | 3.300 | 0.700 | 1.62230 | 53.17 |
| 69 | −1.922 | 0.800 | 1.77250 | 49.60 |
| 70 | 1.922 | 0.700 | 1.62230 | 53.17 |
| 71 | −3.300 | 1.000 | | |
| 72 | ∞ | 13.848 | 2.24000 | 23.50 |
| 73 | −9.886 | 1.380 | | |
| 74 | ∞ | 5.825 | | |
| 75 | 9.745 | 1.110 | 1.84666 | 23.78 |
| 76 | 3.281 | 2.930 | 1.67003 | 47.23 |
| 77 | −6.202 | 3.820 | | |
| 78 | ∞ | 3.000 | 1.76819 | 71.79 |
| 79 | ∞ | 1.150 | | |
| 80 | ∞ | | | |

EXAMPLE 3

| No | r | d | nd | vd |
|---|---|---|---|---|
| 1 | ∞ | 0.567 | 1.76820 | 71.79 |
| 2 | ∞ | 0.320 | | |
| 3 | ∞ | 0.150 | 1.88300 | 40.78 |
| 4 | 0.491 | 0.250 | | |
| 5 | ∞ | 1.637 | 1.83481 | 42.72 |
| 6 | ∞ | 3.433 | 1.83481 | 42.72 |
| 7 | −2.634 | 0.700 | | |
| 8 | 2.385 | 1.330 | 1.77250 | 49.60 |
| 9 | −1.218 | 0.620 | 1.78472 | 25.68 |
| 10 | 4.801 | 1.500 | | |
| 11 | −0.675 | 0.400 | 1.83481 | 42.72 |
| 12 | ∞ | 0.010 | 1.51000 | 60.00 |
| 13 | ∞ | 0.970 | 1.78590 | 44.19 |
| 14 | −1.298 | 1.900 | | |
| 15 | ∞ | 3.459 | | |
| 16 | 19.809 | 24.506 | 2.62000 | 61.10 |
| 17 | ∞ | 1.522 | | |
| 18 | 5.355 | 0.830 | 1.61272 | 58.75 |
| 19 | −3.364 | 2.350 | 1.78800 | 47.38 |
| 20 | 3.364 | 0.830 | 1.61272 | 58.75 |
| 21 | −5.355 | 1.522 | | |
| 22 | ∞ | 24.506 | 2.62000 | 61.10 |
| 23 | −19.809 | 3.459 | | |
| 24 | ∞ | 3.459 | | |
| 25 | 19.809 | 24.506 | 2.62000 | 61.10 |
| 26 | ∞ | 1.522 | | |
| 27 | 5.355 | 0.830 | 1.61272 | 58.75 |
| 28 | −3.364 | 2.350 | 1.78800 | 47.38 |
| 29 | 3.364 | 0.830 | 1.61272 | 58.75 |
| 30 | −5.355 | 1.522 | | |
| 31 | ∞ | 24.506 | 2.62000 | 61.10 |
| 32 | −19.809 | 3.459 | | |
| 33 | ∞ | 3.459 | | |
| 34 | 19.809 | 24.506 | 2.62000 | 61.10 |
| 35 | ∞ | 1.522 | | |
| 36 | 5.355 | 0.830 | 1.61272 | 58.75 |
| 37 | −3.364 | 2.350 | 1.78800 | 47.38 |
| 38 | 3.364 | 0.830 | 1.61272 | 58.75 |
| 39 | −5.355 | 1.522 | | |
| 40 | ∞ | 24.506 | 2.62000 | 61.10 |
| 41 | −19.809 | 3.459 | | |
| 42 | ∞ | 3.459 | | |

-continued

| No | r | d | nd | vd |
|----|---|---|----|----|
| 43 | 19.809 | 24.506 | 2.62000 | 61.10 |
| 44 | ∞ | 1.522 | | |
| 45 | 5.355 | 0.830 | 1.61272 | 58.75 |
| 46 | −3.364 | 2.350 | 1.78800 | 47.38 |
| 47 | 3.364 | 0.830 | 1.61272 | 58.75 |
| 48 | −5.355 | 1.522 | | |
| 49 | ∞ | 24.506 | 2.62000 | 61.10 |
| 50 | −19.809 | 3.459 | | |
| 51 | ∞ | 3.459 | | |
| 52 | 19.809 | 24.506 | 2.62000 | 61.10 |
| 53 | ∞ | 1.522 | | |
| 54 | 5.355 | 0.830 | 1.61272 | 58.75 |
| 55 | −3.364 | 2.350 | 1.78800 | 47.38 |
| 56 | 3.364 | 0.830 | 1.61272 | 58.75 |
| 57 | −5.355 | 1.522 | | |
| 58 | ∞ | 24.506 | 2.62000 | 61.10 |
| 59 | −19.809 | 3.459 | | |
| 60 | ∞ | 8.720 | | |
| 61 | 14.544 | 0.600 | 1.84666 | 23.78 |
| 62 | 4.330 | 1.700 | 1.58267 | 46.42 |
| 63 | −5.583 | 5.170 | | |
| 64 | ∞ | 3.000 | 1.76820 | 71.70 |
| 65 | ∞ | 3.000 | | |
| 66 | ∞ | | | |

COMPARATIVE EXAMPLE

| No | r | d | nd | vd |
|----|---|---|----|----|
| 1 | ∞ | 0.300 | 1.76820 | 64.10 |
| 2 | ∞ | 0.150 | | |
| 3 | ∞ | 0.200 | 1.88300 | 40.76 |
| 4 | 0.492 | 0.100 | | |
| 5 | ∞ | 1.200 | 2.00330 | 28.27 |
| 6 | ∞ | 2.350 | 2.00330 | 28.27 |
| 7 | −2.366 | 0.300 | | |
| 8 | 1.739 | 1.500 | 1.70000 | 48.08 |
| 9 | −1.020 | 2.640 | 1.92286 | 18.90 |
| 10 | −5.875 | 0.850 | | |
| 11 | ∞ | 1.380 | | |
| 12 | 4.669 | 9.784 | 1.58913 | 61.14 |
| 13 | ∞ | 1.000 | | |
| 14 | 3.300 | 0.700 | 1.62230 | 53.17 |
| 15 | −1.922 | 0.800 | 1.77250 | 49.60 |
| 16 | 1.922 | 0.700 | 1.62230 | 53.17 |
| 17 | −3.300 | 1.000 | | |
| 18 | ∞ | 9.784 | 1.58913 | 61.14 |
| 19 | −4.669 | 1.380 | | |
| 20 | ∞ | 1.380 | | |
| 21 | 4.669 | 9.784 | 1.58913 | 61.14 |
| 22 | ∞ | 1.000 | | |
| 23 | 3.300 | 0.700 | 1.62230 | 53.17 |
| 24 | −1.922 | 0.800 | 1.77250 | 49.60 |
| 25 | 1.922 | 0.700 | 1.62230 | 53.17 |
| 26 | −3.300 | 1.000 | | |
| 27 | ∞ | 9.784 | 1.58913 | 61.14 |
| 28 | −4.669 | 1.380 | | |
| 29 | ∞ | 1.380 | | |
| 30 | 4.669 | 9.784 | 1.58913 | 61.14 |
| 31 | ∞ | 1.000 | | |
| 32 | 3.300 | 0.700 | 1.62230 | 53.17 |
| 33 | −1.922 | 0.800 | 1.77250 | 49.60 |
| 34 | 1.922 | 0.700 | 1.62230 | 53.17 |
| 35 | −3.300 | 1.000 | | |
| 36 | ∞ | 9.784 | 1.58913 | 61.14 |
| 37 | −4.669 | 1.380 | | |
| 38 | ∞ | 1.380 | | |
| 39 | 4.669 | 9.784 | 1.58913 | 61.14 |
| 40 | ∞ | 1.000 | | |
| 41 | 3.300 | 0.700 | 1.62230 | 53.17 |
| 42 | −1.922 | 0.800 | 1.77250 | 49.60 |

-continued

| No | r | d | nd | vd |
|----|---|---|----|----|
| 43 | 1.922 | 0.700 | 1.62230 | 53.17 |
| 44 | −3.300 | 1.000 | | |
| 45 | ∞ | 9.784 | 1.58913 | 61.14 |
| 46 | −4.669 | 1.380 | | |
| 47 | ∞ | 1.380 | | |
| 48 | 4.669 | 9.784 | 1.58913 | 61.14 |
| 49 | ∞ | 1.000 | | |
| 50 | 3.300 | 0.700 | 1.62230 | 53.17 |
| 51 | −1.922 | 0.800 | 1.77250 | 49.60 |
| 52 | 1.922 | 0.700 | 1.62230 | 53.17 |
| 53 | −3.300 | 1.000 | | |
| 54 | ∞ | 9.784 | 1.58913 | 61.14 |
| 55 | −4.669 | 1.380 | | |
| 56 | ∞ | 1.380 | | |
| 57 | 4.669 | 9.784 | 1.58913 | 61.14 |
| 58 | ∞ | 1.000 | | |
| 59 | 3.300 | 0.700 | 1.62230 | 53.17 |
| 60 | −1.922 | 0.800 | 1.77250 | 49.60 |
| 61 | 1.922 | 0.700 | 1.62230 | 53.17 |
| 62 | −3.300 | 1.000 | | |
| 63 | ∞ | 9.784 | 1.58913 | 61.14 |
| 64 | −4.669 | 1.380 | | |
| 65 | ∞ | 1.380 | | |
| 66 | 4.669 | 9.784 | 1.58913 | 61.14 |
| 67 | ∞ | 1.000 | | |
| 68 | 3.300 | 0.700 | 1.62230 | 53.17 |
| 69 | −1.922 | 0.800 | 1.77250 | 49.60 |
| 70 | 1.922 | 0.700 | 1.62230 | 53.17 |
| 71 | −3.300 | 1.000 | | |
| 72 | ∞ | 9.784 | 1.58913 | 61.14 |
| 73 | −4.669 | 1.380 | | |
| 74 | ∞ | 1.380 | | |
| 75 | 4.669 | 9.784 | 1.58913 | 61.14 |
| 76 | ∞ | 1.000 | | |
| 77 | 3.300 | 0.700 | 1.62230 | 53.17 |
| 78 | −1.922 | 0.800 | 1.77250 | 49.60 |
| 79 | 1.922 | 0.700 | 1.62230 | 53.17 |
| 80 | −3.300 | 1.000 | | |
| 81 | ∞ | 9.784 | 1.58913 | 61.14 |
| 82 | −4.669 | 1.380 | | |
| 83 | ∞ | 1.380 | | |
| 84 | 4.669 | 9.784 | 1.58913 | 61.14 |
| 85 | ∞ | 1.000 | | |
| 86 | 3.300 | 0.700 | 1.62230 | 53.17 |
| 87 | −1.922 | 0.800 | 1.77250 | 49.60 |
| 88 | 1.922 | 0.700 | 1.62230 | 53.17 |
| 89 | −3.300 | 1.000 | | |
| 90 | ∞ | 9.784 | 1.58913 | 61.14 |
| 91 | −4.669 | 1.380 | | |
| 92 | ∞ | 8.552 | | |
| 93 | 14.544 | 0.600 | 1.84666 | 23.78 |
| 94 | 4.330 | 1.700 | 1.58267 | 46.42 |
| 95 | −5.583 | 5.170 | | |
| 96 | ∞ | 3.000 | 1.76820 | 71.70 |
| 97 | ∞ | | | |

In the aforesaid inventive examples, sufficient antireflection effects are achievable even with a single layer coating, because the vitreous material of the rod lenses in the relay lens system has a high refractive index. And at a specific wavelength, the reflectivity can be reduced down to almost zero. The single layer coating is also cost effective.

It is preferable that the vitreous material used with the inventive rigid endoscope is an eco-friendly glass free of lead and arsenic.

I claim:

1. A rigid endoscope comprising a rigid endoscope optical system having an elongate insert and adapted to implement image transfer using a relay lens, characterized in that said relay lens comprises at lest two rod lenses and satisfies the following three conditions:

$$nd > 2 \quad (1)$$

where nd stands for a refractive index on d-line basis of each of said rod lenses in the said relay lens $$0.05 < \phi \cdot nd/L < 0.1 \quad (2)$$

$$30 < L/\phi < 40 \quad (3)$$

where $\phi$ stands for an outer diameter of said relay lens, and L stands for an optical full length of said relay lens.

2. The rigid endo scope according to claim 1, characterized in that a material used for said rod lens satisfies the following conditions:

$$\tau(350) \geq 75(\%) \quad (4)$$

$$\tau(320) \geq 30(\%) \quad (5)$$

where $\tau(350)$ represents an internal transmittance at a wavelength of 350 nm per 10 mm of the optical material used for said rod lens, and $\tau(320)$ represents an internal transmittance at a wavelength of 320 nm per 10 mm of the optical material used for said rod lens.

3. The rigid endoscope according to claim 1, characterized in that a material used for said rod lens further satisfies the following conditions:

$$Nh < 1,000 \quad (6)$$

$$E > 900 \times 10^8 \, N/m^2 \quad (7)$$

where Nh represents a Knoop hardness, and E represents a Young's modulus.

* * * * *